US009757232B2

(12) United States Patent
Peterson et al.

(10) Patent No.: US 9,757,232 B2
(45) Date of Patent: Sep. 12, 2017

(54) CRIMPING APPARATUS FOR CRIMPING PROSTHETIC VALVE WITH PROTRUDING ANCHORS

(71) Applicant: Edwards Lifesciences Corporation, Irvine, CA (US)

(72) Inventors: Matthew A. Peterson, Newport Beach, CA (US); Robert C. Taft, Irvine, CA (US); Devin H. Marr, Newport Beach, CA (US); Minh T. Ma, Santa Ana, CA (US); Seung-Beom Yi, Mission Viejo, CA (US); Ryan Silva, Folsom, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 101 days.

(21) Appl. No.: 14/707,607

(22) Filed: May 8, 2015

(65) Prior Publication Data

US 2015/0336150 A1 Nov. 26, 2015

Related U.S. Application Data

(60) Provisional application No. 62/002,003, filed on May 22, 2014.

(51) Int. Cl.
*B21D 11/08* (2006.01)
*B21D 39/04* (2006.01)
(Continued)

(52) U.S. Cl.
CPC .............. *A61F 2/2427* (2013.01); *A61F 2/24* (2013.01); *A61F 2/2418* (2013.01); *B21D 11/08* (2013.01);
(Continued)

(58) Field of Classification Search
CPC ..... B25B 27/10; B25B 27/146; B21D 39/048; B21D 39/04; B21D 41/04; B21D 41/05;
(Continued)

(56) References Cited

U.S. PATENT DOCUMENTS 1,438,681 A 12/1922 Bath
1,493,515 A 5/1924 Berthold
(Continued)

FOREIGN PATENT DOCUMENTS

WO WO-03/047468 A1 6/2003

OTHER PUBLICATIONS

P. 8 of applicant's argument.*
(Continued)

*Primary Examiner* — Peter DungBa Vo
*Assistant Examiner* — John S Lowe
(74) *Attorney, Agent, or Firm* — Klarquist Sparkman LLP (57) ABSTRACT

Embodiments of an apparatus, and a method for crimping expandable stents or prosthetic valves having a radially expandable and compressible annular body and one or more protruding anchors extending from the body using the apparatus, where the apparatus comprise a housing, a plurality of circumferentially arranged nesting jaws, and an actuator configured to move the jaws radially inwardly to reduce the size of the crimping aperture, thereby radially compressing the annular body of the prosthetic valve or stent. In particular embodiments, a selected set of the jaws, each having a front side and a recessed portion in its front side adjacent to its inner end. The recessed portions of the selected jaws collectively are sized and shaped to receive the one or more anchors of the prosthetic valve when the annular body is positioned within the crimping aperture.

19 Claims, 10 Drawing Sheets

(51) Int. Cl.
*A61F 2/24* (2006.01)
*B21D 37/00* (2006.01)
*A61F 2/95* (2013.01)

(52) U.S. Cl.
CPC .......... *B21D 37/00* (2013.01); *B21D 39/048* (2013.01); *A61F 2002/9522* (2013.01); *A61F 2230/005* (2013.01); *A61F 2230/0013* (2013.01)

(58) Field of Classification Search
CPC ...... B23P 11/00; A61F 2/2418; A61F 2/2475; A61F 2/2463; A61F 2/82; H01R 43/04; H01R 43/048; Y10T 29/53996; Y10T 29/49927
See application file for complete search history.

(56) References Cited

U.S. PATENT DOCUMENTS

| | | | |
|---|---|---|---|
| 2,079,498 | A | 5/1937 | Douglas |
| 2,787,925 | A | 4/1957 | Buchanan et al. |
| 2,974,367 | A | 3/1961 | Doering et al. |
| 4,350,036 | A | 9/1982 | Valente |
| 5,411,521 | A | 5/1995 | Putnam et al. |
| 5,626,604 | A | 5/1997 | Cottone, Jr. |
| 5,749,921 | A | 5/1998 | Lenker et al. |
| 5,810,873 | A | 9/1998 | Morales |
| 5,836,952 | A | 11/1998 | Davis et al. |
| 5,913,871 | A | 6/1999 | Werneth et al. |
| 5,992,000 | A | 11/1999 | Humphrey et al. |
| 6,009,614 | A | 1/2000 | Morales |
| 6,074,381 | A | 6/2000 | Dinh et al. |
| 6,082,990 | A | 7/2000 | Jackson et al. |
| 6,167,605 | B1 | 1/2001 | Morales |
| 6,309,383 | B1 | 10/2001 | Campbell et al. |
| 6,352,547 | B1 | 3/2002 | Brown et al. |
| 6,360,577 | B2 | 3/2002 | Austin |
| 6,387,117 | B1 | 5/2002 | Arnold, Jr. et al. |
| 6,558,418 | B2 | 5/2003 | Carpentier et al. |
| 6,618,921 | B1 | 9/2003 | Thornton |
| 6,629,350 | B2 | 10/2003 | Motsenbocker |
| 6,651,478 | B1 | 11/2003 | Kokish |
| 6,682,553 | B1 | 1/2004 | Webler, Jr. |
| 6,730,118 | B2 | 5/2004 | Spenser et al. |
| 6,769,161 | B2 | 8/2004 | Brown et al. |
| 6,823,576 | B2 | 11/2004 | Austin |
| 6,840,081 | B2 | 1/2005 | Kokish |
| 6,889,579 | B1 | 5/2005 | Brown |
| 6,915,560 | B2 | 7/2005 | Austin |
| 6,920,674 | B2 | 7/2005 | Thornton |
| 6,925,847 | B2 | 8/2005 | Motsenbocker |
| 6,931,899 | B2 | 8/2005 | Goff et al. |
| 6,968,607 | B2 | 11/2005 | Motsenbocker |
| 6,988,881 | B2 | 1/2006 | Motsenbocker et al. |
| 7,010,953 | B2 | 3/2006 | Stupecky |
| 7,021,114 | B2 | 4/2006 | Perreault |
| 7,069,794 | B2 | 7/2006 | Motsenbocker et al. |
| 7,096,554 | B2 | 8/2006 | Austin et al. |
| 7,143,625 | B2 | 12/2006 | Edin |
| 7,152,452 | B2 | 12/2006 | Kokish |
| 7,207,204 | B2 | 4/2007 | Weber et al. |
| 7,225,518 | B2 | 6/2007 | Eidenschink et al. |
| 7,284,401 | B2 | 10/2007 | Larson et al. |
| 7,389,670 | B1 | 6/2008 | Kokish et al. |
| 7,415,861 | B2 | 8/2008 | Sokel |
| 7,487,579 | B2 | 2/2009 | Eidenschink et al. |
| 7,530,253 | B2 | 5/2009 | Spenser et al. |
| 7,587,801 | B2 | 9/2009 | Austin |
| 7,628,051 | B1 | 12/2009 | Kokish et al. |
| 7,895,876 | B2 | 3/2011 | Spenser et al. |
| 7,967,138 | B2 | 6/2011 | Ryan et al. |
| 8,006,535 | B2 | 8/2011 | Righini et al. |
| 8,042,373 | B2 * | 10/2011 | Stenzel ..................... A61F 2/82 72/402 |
| 8,112,857 | B2 | 2/2012 | Voelkl |
| 8,312,614 | B2 | 11/2012 | Sokel |
| 8,438,895 | B2 * | 5/2013 | Perreault ................... A61F 2/95 29/283.5 |
| 8,479,380 | B2 * | 7/2013 | Malewicz ............. A61F 2/2427 29/760 |
| 8,640,521 | B2 | 2/2014 | Righini et al. |
| 2003/0192164 | A1 | 10/2003 | Austin |
| 2006/0213049 | A1 | 9/2006 | Serrano et al. |
| 2007/0056346 | A1 | 3/2007 | Spenser et al. |
| 2007/0061009 | A1 | 3/2007 | Spenser et al. |
| 2009/0043249 | A1 | 2/2009 | Sokel |
| 2010/0292780 | A1 | 11/2010 | Straubinger et al. |
| 2012/0239142 | A1 | 9/2012 | Liu et al. |

OTHER PUBLICATIONS

Int'l. Search Report issued in PCT/US2015/030507, dated Aug. 3, 2015.
http://www.machinesolutions.org/custom.sub.--tools.sub.--equipment/HV200.h- tm, 2 pages, Aug. 22, 2006.
http://www.machinesolutions.org/custom.sub.--tools.sub.--equipment/HV200.s- ub.--specs.htm, 1 page, Aug. 22, 2006.

* cited by examiner

CRIMPING APPARATUS FOR CRIMPING PROSTHETIC VALVE WITH PROTRUDING ANCHORS

CROSS-REFERENCE TO RELATED APPLICATION

The present application claims the benefit to U.S. Provisional Application No. 62/002,003, filed May 22, 2014, which is incorporated herein by reference.

FIELD

The present disclosure relates to a crimping apparatus and, more particularly, to an apparatus for crimping a stent or stented prosthetic valve having a protruding anchor member, such as a prosthetic heart valve, from a large diameter to a smaller diameter.

BACKGROUND

In recent years, a variety of prosthetic valves have been developed wherein a valve structure (e.g., tissue leaflets) is mounted on a metal stent and then delivered to a treatment site via a catheterization technique. Such transcatheter prosthetic valves may be self-expandable or balloon expandable. Balloon-expandable prosthetic valves are typically crimped from an initial large diameter to a smaller diameter prior to advancement to a treatment site in the body. Before crimping, a balloon expandable prosthetic valve is typically placed over an inflatable balloon on a catheter shaft. In cases where the prosthetic valve was manufactured in its fully crimped diameter, the prosthetic valve is expanded and then crimped on the balloon. Once delivered to the implantation site, the balloon can be inflated to expand the prosthetic valve to its fully functional size. Self-expanding prosthetic valves are typically also crimped to a smaller diameter, but are then inserted into a sheath. After placement in the body, the sheath is withdrawn, and the prosthetic valve expands inside the body.

A known type of crimping apparatus for crimping a prosthetic valve includes a plurality of circumferentially arranged moveable segments that define a variable diameter crimping aperture. When a prosthetic valve is placed in the crimping aperture, the moveable segments are moved radially inwardly to decrease the diameter of the crimping aperture, thereby radially compressing the prosthetic valve. Some prosthetic valves have protruding members or anchors that extend outwardly from the annular main body of the prosthetic valve. Such anchors may not be designed to be subjected to the crimping forces of the crimping apparatus, and in fact, do not need to crimped along with the main body of the prosthetic valve. Thus, it is desirable to achieve crimping of the main body of the prosthetic valve without subjecting the anchors that extend from the main body to any crimping forces and without exerting undue mechanical stresses on the anchors.

SUMMARY

The present invention pertains to embodiments of a method and an apparatus for crimping expandable stents or prosthetic valves having a radially expandable and compressible annular body and one or more protruding anchors extending from the body. In an exemplary embodiment, the apparatus comprises a housing; a plurality of circumferentially arranged, nesting jaws; and an actuator configured to move the jaws radially inwardly to reduce the size of the crimping aperture, thereby radially compressing the annular body of the prosthetic valve or stent. The jaws can be axially and rotatably constrained by the housing but are radially movable, and each jaw comprises an inner end that has a partial crimping surface that combines with the respective surface on the other jaws to form a crimping aperture of variable diameter. The apparatus may also comprise a selected set of the jaws, each having a front side and a recessed portion in its front side adjacent to its inner end. The recessed portions of the selected jaws collectively are sized, shaped, and positioned to receive the one or more anchors of the prosthetic valve when the annular body is positioned within the crimping aperture. In some embodiments, the selected set of jaws includes all of the jaws. In other embodiments, the selected set of the jaws comprises a plurality of groups of jaws that are spaced circumferentially around the crimping aperture, for example, evenly spaced. In certain examples, there are two groups of jaws on opposing sides of the crimping aperture.

In some embodiments, the recessed portion of each of the selected jaws is defined by a surface that extends from the front side of the jaw toward a back side of the jaw. Typically, the angle between the partial crimping surface and the surface of the recessed portion is between 5 to 85 degrees, more typically between 10 to 70 degrees.

In some embodiments, the apparatus also includes a plurality of slidable shielding members that are disposed within the recessed portions of the selected jaws. Typically, each shielding member is sized and shaped to engage one of the anchors of the prosthetic valve when the annular body is positioned within the crimping aperture. Each shielding member is configured to move radially inwardly when the actuator is actuated to move the jaws radially inwardly. In certain embodiments, there are two shielding members, located on diametrically opposing sides of the crimping aperture.

In another representative embodiment, a crimping apparatus comprises crimping means for crimping the annular body of a prosthetic valve or stent to a radially compressed state while retaining the anchors of the prosthetic valve at an angle less than 90 degrees relative to the annular body such that a crimping force is applied only to the annular body, and an actuating means for moving the crimping means radially inwardly, thereby crimping the annular body without crimping the anchors.

In some embodiments, the crimping means comprises a plurality of circumferentially arranged jaws defining a variable crimping aperture for receiving the annular body of the prosthetic valve. In certain embodiments, there is a selected set of the jaws, each jaw having a front side, an inner end, and a recessed portion in the front side adjacent to the inner end. Typically, the recessed portions collectively are sized and shaped to receive the anchors at an angle of less than 90 degrees relative to the annular body.

In some embodiments, the apparatus also comprises a means for preventing the protruding anchors from contacting the jaws during crimping.

Also disclosed herein is a method of using the disclosed crimping apparatus. In some embodiments, the method comprises placing the annular body of a prosthetic valve or stent into the variable aperture formed by a plurality of jaws. The anchors of the prosthetic valve or stent are located or positioned in recessed portions of a selected set of the plurality of jaws. The annular body can then be crimped with the jaws. In some embodiments, the protruding anchors can be placed against slidable shielding members that are located in the recessed portions of the selected set of the plurality of jaws.

After crimping, the prosthetic valve can be loaded onto a delivery device. In some embodiments, loading the prosthetic valve onto the delivery device comprises inserting the annular body into an inner sheath of the delivery device, and inserting the anchors into an outer sheath, which extends coaxially over the inner sheath.

In another aspect, a crimping accessory tool comprises a handle and one or more fingers configured to be placed inside of a prosthetic valve in the space between the outer surface of the leaflets and the inside of the frame of the prosthetic valve. The one or more fingers are sized and shaped to prevent the leaflets from rubbing against the frame or extending through openings of the frame, thereby protecting the leaflets against damage caused by contact with the frame during the crimping process.

The foregoing and other objects, features, and advantages of the invention will become more apparent from the following detailed description, which proceeds with reference to the accompanying figures.

DETAILED DESCRIPTION

The present disclosure provides an improved crimper for stents or prosthetic valves (e.g., prosthetic heart valves), particularly those with one or more protruding anchors that extend outwardly from the main body of the stent or the prosthetic valve. The particularly advantageous features of the present crimper enable reduction in diameter of relatively large stents or prosthetic valves while minimizing the stress imposed on the anchors. The crimper is especially suited for crimping prosthetic heart valves that have expanded diameters significantly larger than most stents currently in use. According to Chessa, et al., the Palmaz® Genesis® XD stents (Cordis Corp. Bridgewater, N.J.) are designed for an expansion range of 10-18 mm, and are considered as either large or extra-large stents (see, Results and Mid-long-term Follow-up of Stent Implantation for Native and Recurrent Coarctation of the Aorta, *European Heart Journal*, V. 26, No. 24, Pp. 2728-2732, published online Sep. 26, 2005). The most frequently used stents are significantly smaller, in the 3-6 mm range. Crimpers for these smaller stents have proved inadequate for reducing in size even larger prosthetic valves, such as the stented prosthetic heart valves. Conversely, aspects of the present crimper may be applicable for use in crimping stents as well, although certain features described herein make it particularly well-suited for crimping large diameter stents, stent grafts, and prosthetic valves.

Figure 9:
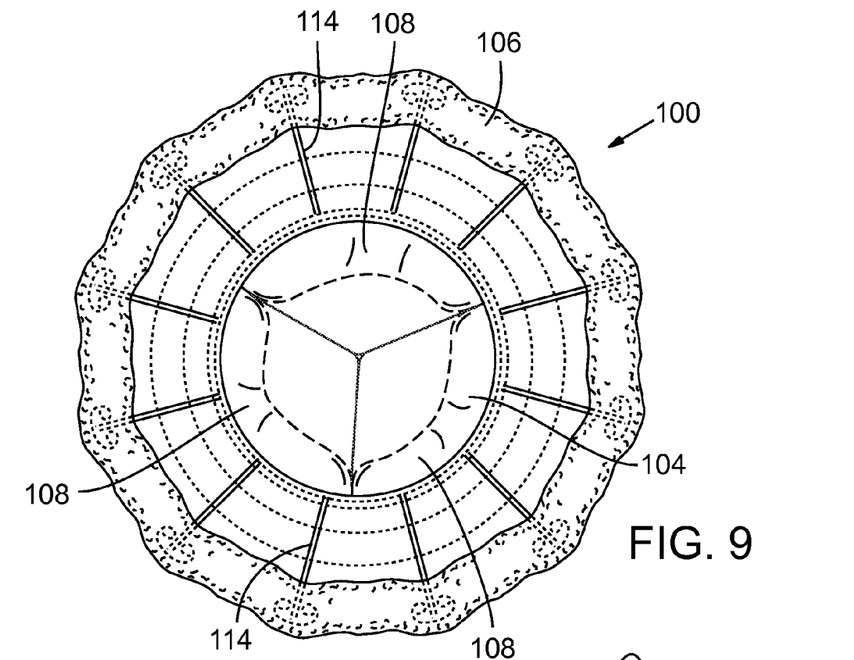
FIG. 9 is a top view of an exemplary prosthetic heart valve that can be crimped using the crimping apparatus of FIG. 1.
Figure 10:
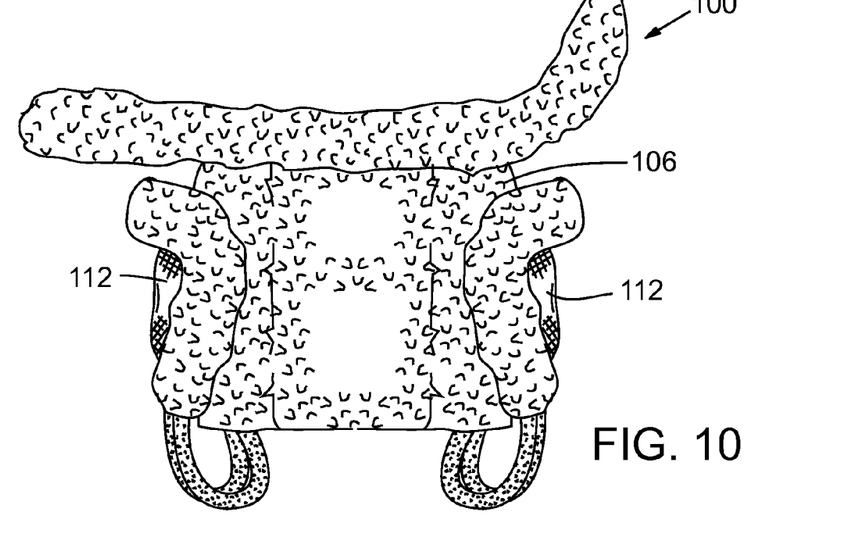
FIG. 10 is a side view of an exemplary prosthetic heart valve.
Figure 11:
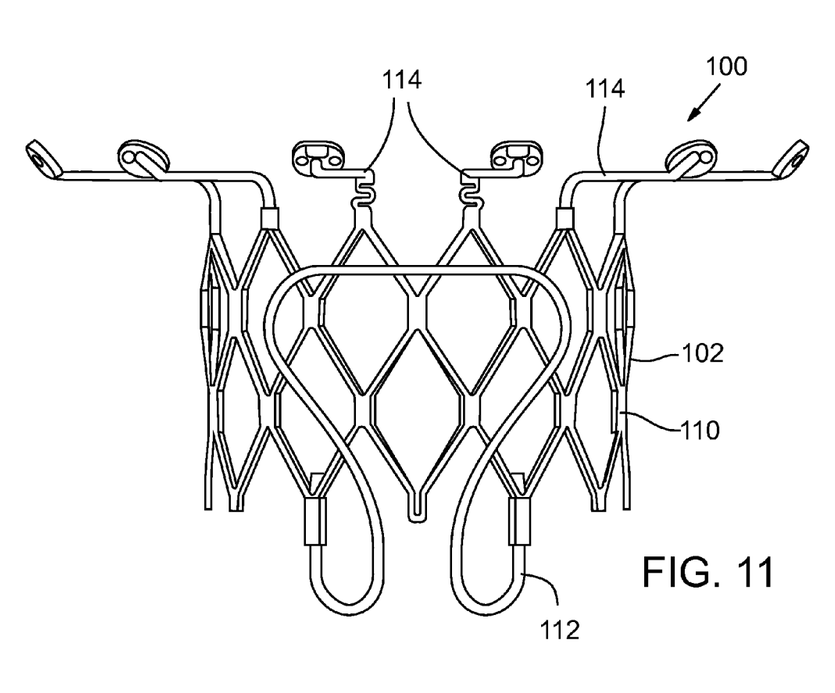
FIG. 11 is a side view of the bare frame of the prosthetic heart valve of FIG. 9.

The term "stented prosthetic valve" as used herein refers to prosthetic valves for implant, primarily prosthetic heart valves but also venous valves and the like. A stented prosthetic valve has a support frame or stent that provides primary structural support in its expanded state. Such support frames are typically tubular when expanded, and may be expanded using a balloon or due to their own inherent elasticity (i.e., self-expanding). Exemplary stented prosthetic valve are illustrated in FIGS. 9-11, although the disclosed embodiments can be used for crimping other such prosthetic valves.

Figure 1:
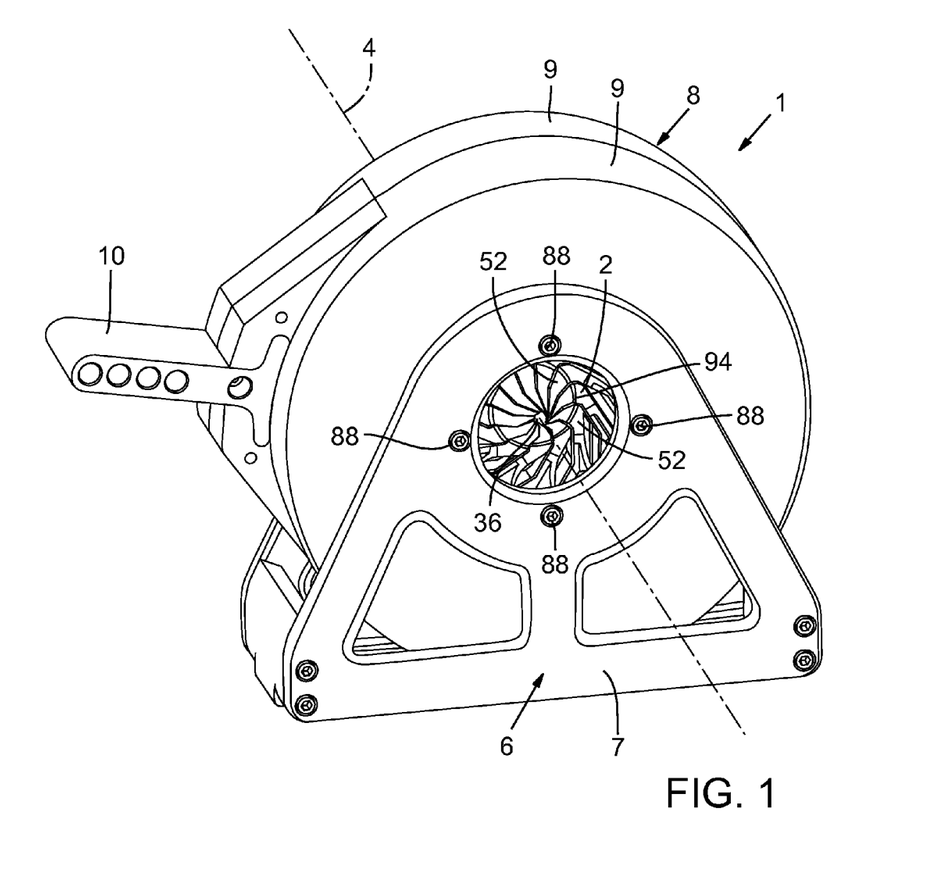
FIG. 1 is a perspective view illustrating one embodiment of a crimping apparatus.

With reference to FIG. 1, an exemplary embodiment of an improved prosthetic valve or stent crimping mechanism 1 (also referred to herein as a "crimping apparatus") is shown. The crimping mechanism 1 in the illustrated embodiment is formed from a plurality of nested jaws 2 (twelve in the illustrated embodiment) arranged around a central axis 4 of the jaws. The jaws 2 are shown in a "closed" position in FIG. 1 defining a variable-sized crimping aperture 36 (FIGS. 2 and 3) between their inner ends. The crimping mechanism 1 has a stationary frame 6 which can act as a stand or base. The jaws 2 are located within a rotating portion comprising a two-part outer housing 8 comprising end caps 9, and an actuator in the form of a lever or handle 10 connected to and extending from the end caps 9. Each end cap 9 of the outer housing 8 comprises a generally disk-shape with a radially-oriented circular wall and an annular outer rim extending toward the opposite housing part. The outer rims of the end caps 9 can contact one another and surround the internal mechanism circumferentially. In other embodiments, the outer rims of the end caps 9 do not contact each other, for example, contacting one or more other outer housing components, for example, a shell.

Figure 2:
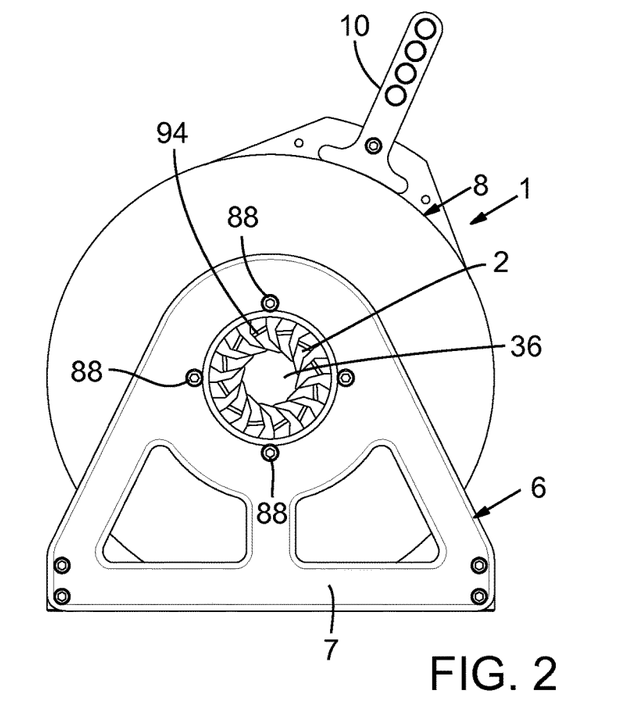
FIG. 2 is a side elevation view of the crimping apparatus of FIG. 1, illustrating the crimping aperture when the jaws of the crimping apparatus are in their open positions.
Figure 3:
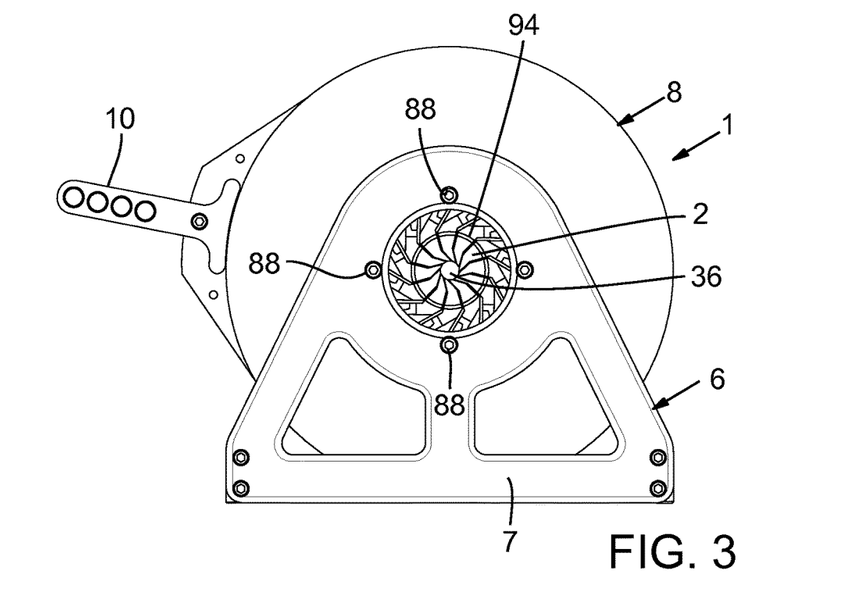
FIG. 3 is a side elevation view of the crimping apparatus of FIG. 1, illustrating the crimping aperture when the jaws are in their closed positions.

FIGS. 2 and 3 show side views of the crimping apparatus 1. FIG. 2 shows the crimping apparatus 1 in an "open" position, with the jaws 2 moved to their radially outward position such that the aperture 36 has a relatively large diameter for receiving a prosthetic valve in a fully expanded state. The "open" or radially expanded position means that the jaws are moved radially outward from each other far enough to allow an annular body in an expanded state to be inserted into the crimping aperture. FIG. 3 shows the jaws 2 in a "closed" or constricted position, such that the aperture 36 has a smaller diameter. The "closed" or radially contracted position means that the jaws are moved radially inward toward each other to radially compress the annular body in the crimping aperture.

Figure 4:
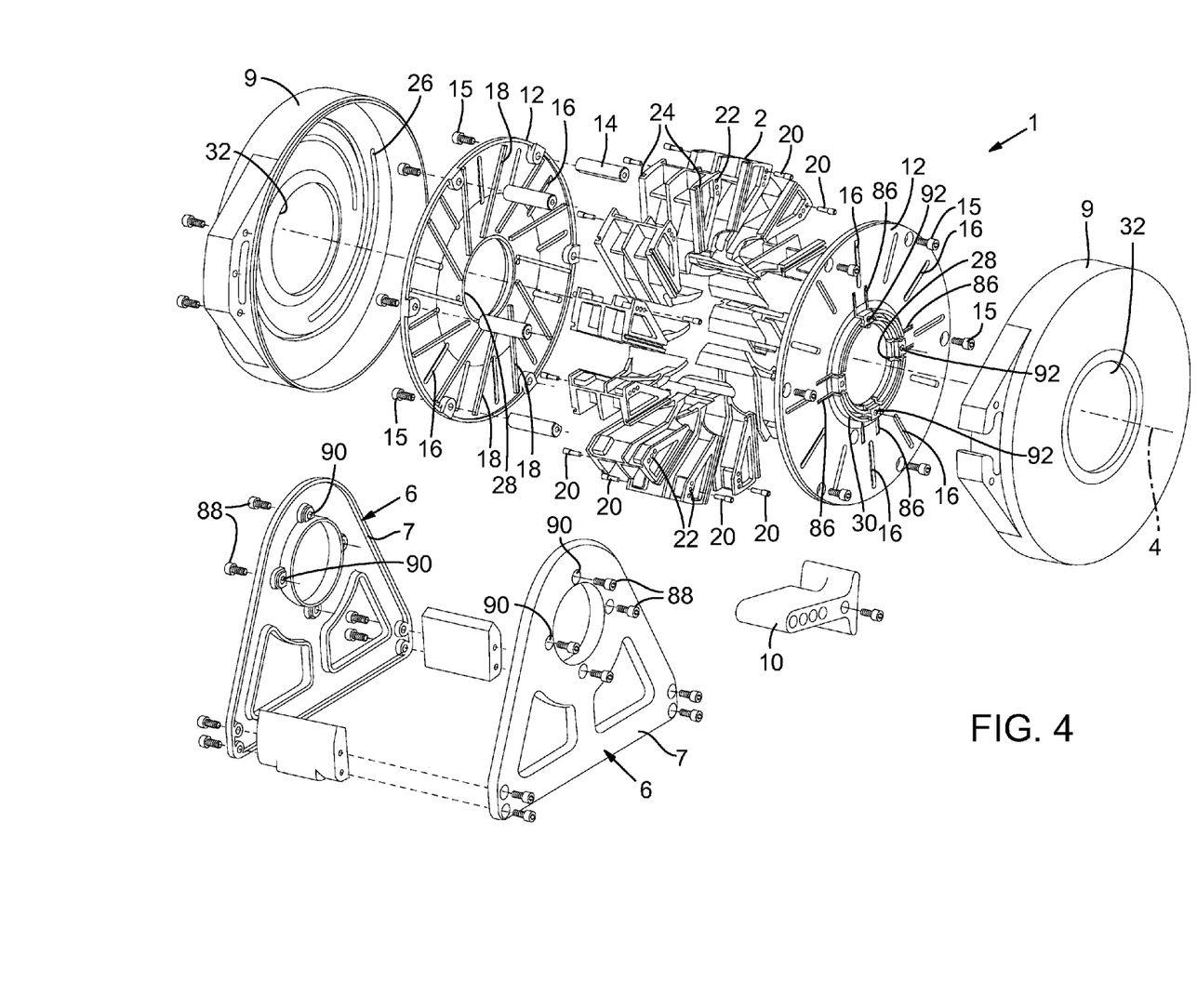
FIG. 4 is an exploded, perspective view showing the components of the crimping apparatus of FIG. 1.

FIG. 4 shows an exploded view of the crimper mechanism 1. In FIG. 4 it can be seen that the jaws 2 are arranged about the central axis 4 and that the jaws are flanked on both sides by two end plates 12. Each end plate 12 in the illustrated embodiment is disk-shaped and can be connected to each other by spacers 14 (six in the illustrated embodiment) that are spaced around the circumferential edge of the inner plates 12, and that surround the jaws 2 circumferentially. The spacers 14 can be secured to the inner plates 12 by a plurality of screws 15, each of which extends through a corresponding opening in a plate 12 and is tightened into a corresponding threaded opening in one end of the corresponding spacer 14. The assembly of the two inner plates 12 and the spacers 14 therefore defines a generally cylindrical cavity that contains the jaws 2. The axial dimensions of the jaws 2 and lengths of the spacers 14 are such that the jaws are axially and rotatably constrained between the inner faces of the inner plates 12, but have sufficient clearance to enable sliding movement of the jaws therein.

Each inner plate 12 in the illustrated embodiment further comprises a plurality of spoke-like channels 16, one for each jaw 2 (twelve in the illustrated embodiment), which are evenly spaced and arranged on radial lines extending outward from the center of the inner plates 12. Each inner plate 12 also comprises a plurality of guide tabs 18, each corresponding to and offset from a respective channel 16. As can be seen in FIG. 4 and in detail in FIGS. 6 and 7, each jaw 2 is provided with a pair of camming members or pegs 20, one projecting outwardly from each axial side of each jaw. In particular embodiments, these pegs 20 are located in one of three holes 22 on each axial side of the jaw 2, the holes 22 being on a radial line from the center axis 4 and being located near the radially outermost edge of the jaw 2. The positioning of the pegs 20 in the holes is described in greater detail below. Each jaw 2 further comprises a pair of radially extending guide slots 24 (one on each axial side of the jaw) that are offset from the camming members 20. The guide slots 24 engage with the guide tabs 18 on the inner plates 12, while the camming members 20 pass through the channels 16 and interact with spiral channels 26 located in the end caps 9 of the outer housing 8, as discussed in greater detail below.

The number of jaws desirably, although not necessarily, ranges between 6 and 12, although a greater or fewer number of jaws can be used. In the illustrated embodiment, each inner plate 12 has one channel 16 for each jaw and each jaw 2 has two guide slots 24. The fewer jaws, the larger each one would be to provide the necessary contributory crimping surface in the aperture. Moreover, decreasing the number of jaws affects the circularity of the aperture (with more jaws more closely approximating a circle). On the other hand, including more jaws reduces the size of each jaw and increases the complexity of the apparatus. Ultimately, material strength considerations and cost constrain the number of jaws.

Each inner plate 12 further comprises a central hole or aperture 28 with an axially-oriented rim 30 extending away from the jaws 2. The rim 30 extends through a center hole or aperture 32 of an adjacent end cap 9, and engages an adjacent side portion 7 of the stand 6, such that the outer housing 8 is between the side portions 7 of the stand 6 and the inner plates 12, and can rotate relative to the inner plates 12. Each inner plate 12 can be secured to a respective side portion 7 of the stand 6 with a plurality of screws 88 that extend through corresponding openings 90 in the side portion 7 and are tightened into corresponding threaded openings 92 in the inner plate 12. Consequently, rotating lever 10 causes corresponding rotation of the outer housing 8 relative to the stand 6 and the inner plates 12.

Figure 5:
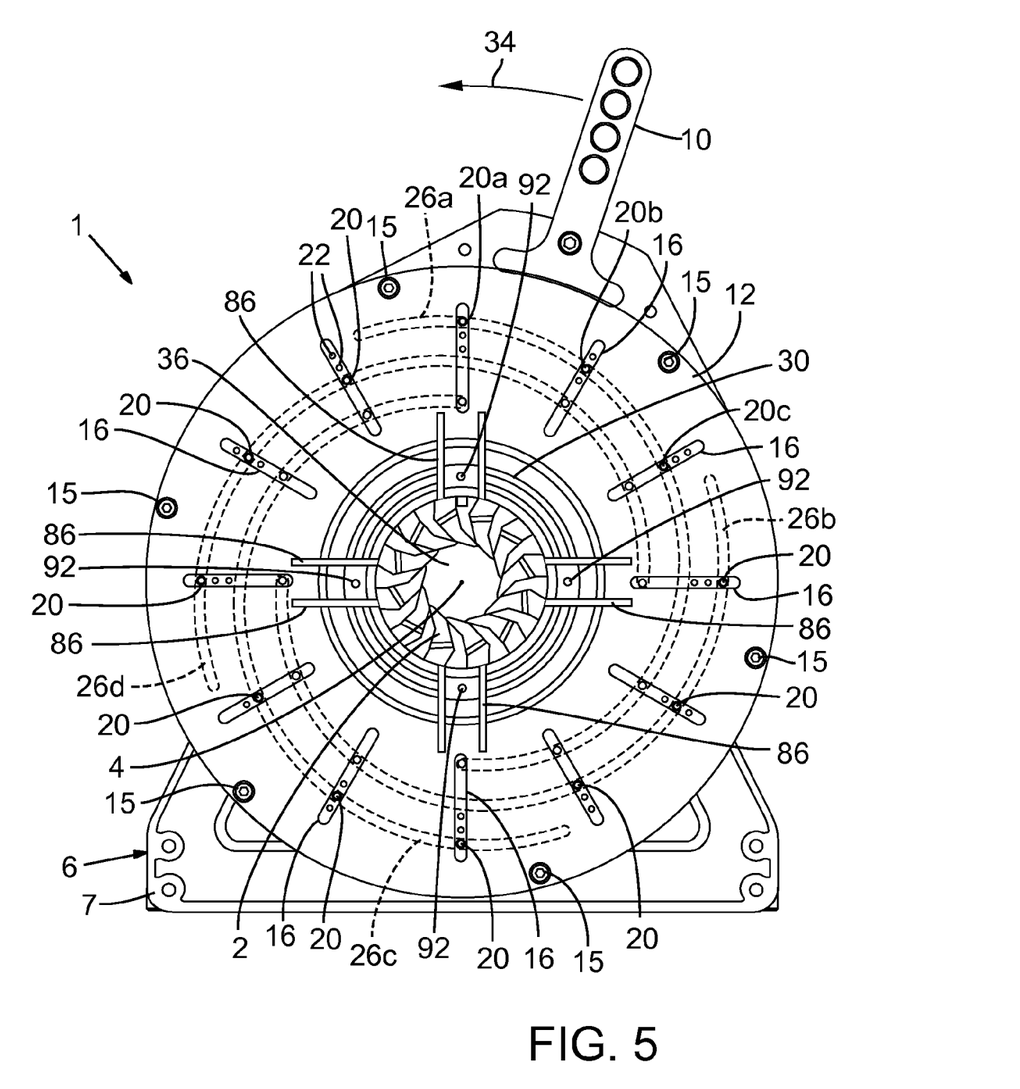
FIG. 5 is a side elevation view of the crimping apparatus of FIG. 1 with a side portion of the base removed illustrating the spiral tracks, channels, and camming members configured for moving the jaws.

FIG. 5 provides a side view of the crimping apparatus 1 with the near side portion 7 of the stationary frame 6 and near side portion 9 of outer housing 8 removed for clarity, and indicates in phantom the position of the four independent spiral channels or tracks 26a, 26b, 26c, 26d located on the inner surface of an end cap 9. FIG. 5 also indicates the positions of the channels 16 in the adjacent inner plate 12 relative to the spiral channels 26a-26d. As shown, camming members 20 pass through the channels 16 and into the spiral channels 26a-26d. As can be seen in FIG. 5, each spiral channel 26a-26d interacts with three consecutive jaws 2 through their respective camming members 20. The holes 22 that are not occupied by a camming member 20 are also indicated. For example, it can also be seen that, progressing in a clockwise direction starting at the 12:00 position, the first of the three consecutive jaws 2 has a camming member 20a in the radially outermost hole 22 and extending into channel 26a; the second, or middle, jaw has a camming member 20b in the middle hole 22 and extending into channel 26a, and the third jaw has a camming member 20c in the radially innermost hole 22 and extending into channel 26a. Each of the remaining channels 26b, 26c, and 26d similarly interact with a respective set of three consecutive jaws 2.

Upon rotation of the outer housing (counter-clockwise in this view) the spiral tracks 26a-26d apply a generally radially inward camming force to the camming members 20, and therethrough also to the jaws 2. The geometrical constraints produce the radial motion of the camming members 20, and thus the jaws 2, toward the central axis 4. Furthermore, the jaw motion is constrained both by the cooperation of the camming members 20 with the channels 16, as well as by the guide slots 24 sliding over the guide tabs 18 (FIG. 4). When the handle 10 is rotated in the direction of the arrow 34 in FIG. 5, the outer housing 8 rotates, thereby causing the spiral tracks 26 to rotate. This rotational movement of the spiral tracks 26 results in the camming members 20, and therethrough also the jaws 2, moving radially inward, thereby reducing the diameter of the crimping aperture 36 (FIG. 5). In alternative embodiments, only one of the end plates 12 can be provided with slots 16 and/or ridges 18, and the jaws 2 can each be provided with only one camming member 20 and/or groove 24. In addition, in alternative embodiments, additional details of the crimper can be varied, for example, the number of tracks 26 and the arc lengths of the tracks 26, as further described in U.S. Pat. No. 7,530,253, the entirety of which is incorporated herein by reference.

Figure 6:
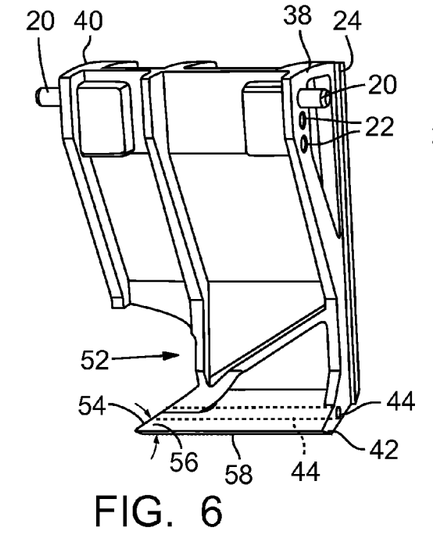
FIG. 6 is a perspective view of a jaw as viewed from the rear and one side thereof.
Figure 7:
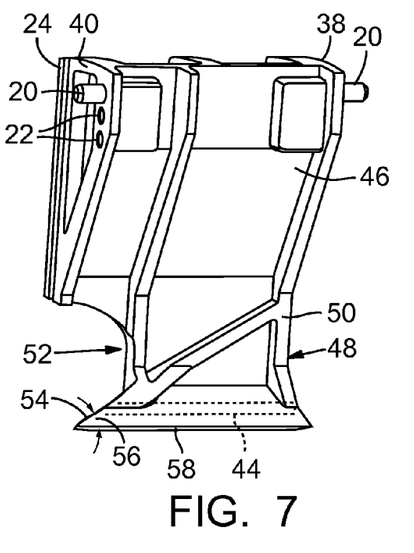
FIG. 7 is a perspective view of a jaw as viewed from the front and one side thereof.

FIGS. 6 and 7 provide two detailed views of a jaw 2. FIG. 6 shows the jaw 2 oriented to show the detail of a back surface or side 38 and FIG. 7 provides a detailed view of a front surface or side 40. With reference to FIGS. 6 and 7, it can be seen that each jaw 2 in the illustrated embodiment comprises three holes 22, one of which is occupied by a camming member 20, and a guide slot 24 on each of the front and back sides. The radially inner end of each jaw defines a wedge-shaped finger 42. Each jaw 2 includes a relatively enlarged head portion 46. A cutout or recess 48 on a lateral surface of the jaw narrows the material between the head portion 46 and the finger 42 to a bridge 50. As can be seen in FIG. 3, when the jaws 2 move radially inward and constrict aperture 36, each jaw 2 nests in the recess 48 of the jaw behind it.

A cutout in the front side 40 of the jaw 2 creates a cavity or recessed portion 52. The recessed portion 52 is defined by a surface 54 that extends from the lowermost forward edge of the finger 42 toward the back side 38 at an angle 56 defined between the surface 54 and the radially innermost or aperture-defining surface 58 of the finger 42. The recessed portion 52 is sized and shaped to receive an anchor of a prosthetic valve during a crimping process to prevent the application of crimping forces to the anchor, as further described in detail below. In particular embodiments, the angle 56 is less than about 90 degrees, such as from about 0 degrees to about 70 degrees, from about 20 degrees to about 60 degrees, or from about 30 degrees to 50 about degrees. The finger 42 can optionally include a reinforcing member 44 extending axially through the finger from back surface 38 to the front surface 40. The reinforcing member 44 can be made of a relatively stiffer and/or stronger material than the jaw itself to strengthen and/or stiffen the area of the jaw adjacent the recess 52. In particular embodiments, for example, the jaws 2 can be made of a polymeric material, such as a molded plastic material, and the reinforcing member 44 can be made of a metal or metal alloy (e.g., stainless steel).

Referring again to FIG. 1, the recessed portions 52 of the jaws 2 collectively define an annular recess or groove 94 that extends along the front surfaces of the jaws 2 through 360 degrees. In use, the radially compressible main body of a prosthetic valve is positioned within the crimping aperture 36 while the anchors protruding from the main body can be positioned within the annular groove 94 to prevent the application of crimping forces to the anchors.

FIGS. 9 and 10 show an exemplary prosthetic heart valve 100 that can be crimped using the crimping apparatus 1. The illustrated prosthetic valve 100 comprises a stent or frame 102 (FIG. 11), a leaflet assembly 104 supported by and secured inside the frame 102 and a cover 106 covering portions of the frame 102. The leaflet assembly 104 can comprise one or more tissue leaflets 108 (three in the illustrated embodiment) made of biological material (e.g., pericardial tissue, such as bovine, porcine or equine pericardial tissue) or synthetic material (e.g., polyurethane). The leaflets 108 are configured to allow blood to flow through the prosthetic valve in one direction and block the flow of blood in the opposite direction. In FIG. 9, the leaflets 108 are shown in solid lines, depicting the closed position for blocking the flow of blood and in dashed lines, depicting the open position allowing blood to flow through the prosthetic valve.

FIG. 11 shows the bare frame 102 (the frame without the leaflets or cover). The frame 102 comprises an annular main body 110 (which houses the leaflet assembly 104), one or more first anchors 112 extending from one end of the main body 110, and one or more second anchors 114 extending from the opposite end of the main body. In the illustrated example, the prosthetic valve 100 comprises a prosthetic mitral valve that is implantable in the native mitral valve annulus, wherein the first anchors 112 comprise ventricular anchors that are deployed behind the native mitral valve leaflets within the left ventricle and the second anchors 114 comprise atrial anchors that are deployed against the mitral annulus within the left ventricle. The illustrated prosthetic mitral valve 100 comprises two ventricular anchors 112 positioned on diametrically opposite sides of outflow end of the main body and twelve atrial anchors 114. In alternative embodiments, the prosthetic valve can include greater or fewer number of ventricular anchors and/or atrial anchors.

The frame 102 can comprise a shape-memory material, such as nitinol (a nickel-titanium alloy) for example, to enable self-expansion from a radially compressed state to an expanded state. When constructed of a self-expanding material, the prosthetic valve can be crimped to the radially compressed state using the crimping apparatus 1 (as further described below) and loaded into a sheath of a delivery catheter for delivery to an implantation site. When released from the sheath, the prosthetic valve can self-expand to the expanded state at the implantation site (e.g., the native mitral valve). In alternative embodiments, the frame 102 can be plastically expandable from a radially compressed state to an expanded state by an expansion device, such as an inflatable balloon (not shown), for example. Such plastically expandable frames can comprise stainless steel, chromium alloys, and/or other suitable materials. When constructed of a plastically expandable material, the prosthetic valve can be crimped using the crimping apparatus 1 to a radially compressed state onto or adjacent a balloon (or other expansion device) of a delivery catheter.

The cover 106 can comprise a blood-impermeable fabric and can extend over the outside of the main body, the atrial anchors 114, and/or portions of the ventricular anchors 112. The fabric can comprise a polyester material, such as polyethylene terephthalate (PET). Alternatively, the cover can comprise biological matter, such as pericardial tissue or other biological tissue. Further details of the prosthetic valve 100, for example, construction and assembly, are disclosed in U.S. Patent Application Publication No. 2011/0137397 A1 and U.S. Patent Publication No. 2014/0222136 A1, both of which are incorporated herein by reference in their entirety.

In the expanded state, the ventricular anchors 112 extend along the outer surface of the main body 106. Thus, once implanted at the native mitral valve, the native mitral valve leaflets can be captured between the main body and ventricular anchors, thereby anchoring the prosthetic valve in place against systolic pressure in the left ventricle. When crimping the prosthetic valve, it is desirable to avoid inserting the ventricular anchors 112 within the crimping aperture to prevent deformation of the ventricular anchors and to ensure even radially crimping of the main body. At the same time, it is desirable to avoid over-stressing the ventricular anchors 112 when positioning them outside of the crimping aperture. To crimp the prosthetic valve 100, the lever 10 is actuated to place the jaws 2 in the open position to increase the size of the crimping aperture 36 (FIGS. 2 and 5). The atrial anchors 114 can be bent or repositioned from their radially extending positions to axially extending positions such that the atrial anchors 114 extend axially from the inflow end of the main body. The atrial anchors 114 and the main body 110 can then be inserted into the crimping aperture 36 and the ventricular anchors 112 can be positioned within the annular groove 94 formed by cavities 52 outside of the crimping aperture.

Figure 8:
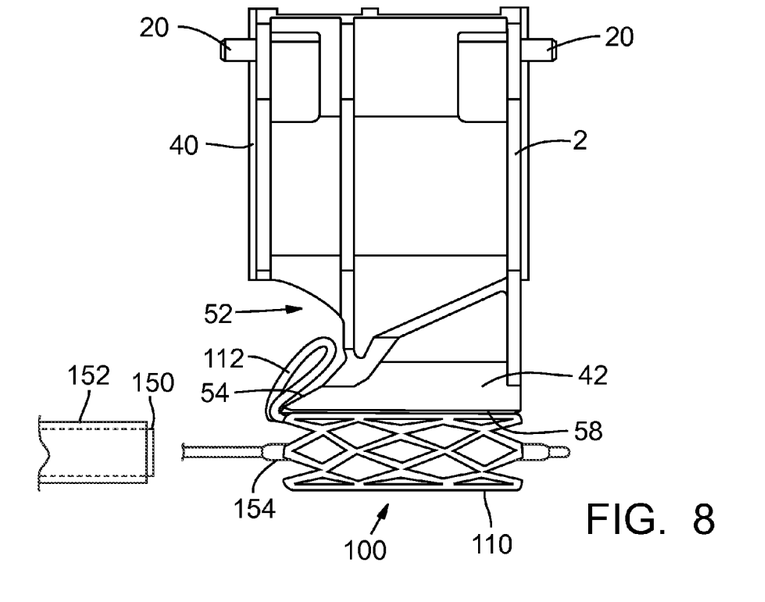
FIG. 8 is a side view of a jaw illustrating how the jaw interacts with a prosthetic valve.

FIG. 8 shows a schematic representation of how a jaw 2 interacts with the prosthetic valve 100. As can be seen, the main body 110 of the prosthetic valve 60 is contact with or adjacent the innermost surface 58 of the finger 42. The ventricular anchor 112 is located in the recessed portion 52 and is optionally in contact with the surface 54 of the recessed portion 52. Once the prosthetic valve is properly positioned relative to the jaws 2, the lever 10 can be actuated to move the jaws radially inwardly against the main body (and the atrial anchors 114 if the prosthetic valve includes such anchors) to the radially constricted position (FIGS. 1 and 3). Moving the jaws 2 against the main body radially compresses the main body (and the atrial anchors) from the expanded state to the radially compressed state. Since the ventricular anchors 112 are disposed outside of the crimping aperture, the ventricular anchors 112 are not compressed by the jaws 2 during the crimping process. Additionally, because the ventricular anchors 112 are held at a relatively small angle relative to the main body (less than about 90 degrees), the anchors 62 are not subject to excessive mechanical stress during the crimping process.

After crimping, the jaws can be opened and the crimped prosthetic valve can be inserted into the sheath of a delivery catheter (where the frame is made of a self-expandable material). In certain embodiments, the main body 110 can be inserted into an inner sheath 150 of a delivery catheter and the anchors 112 can be inserted into an outer sheath 152 of the delivery catheter (between the inner sheath and the outer sheath). Where the frame is made of a plastically expandable material, the distal end portion of the delivery catheter can be disposed within the prosthetic valve during the crimping procedure. In that case, actuating the jaws 2 crimps the prosthetic valve directly onto the distal end portion of the delivery apparatus (e.g., on or adjacent a balloon of the delivery apparatus). FIG. 8, for example, shows the prosthetic valve being crimped onto a balloon 154 of a balloon catheter of a delivery apparatus.

In the illustrated embodiment, each jaw 2 is provided with a recessed portion 52, although this need not be the case. Accordingly, in alternative embodiments, only a selected set of the jaws 2 can include a recessed portion 52, depending on the number and position of anchors on the prosthetic valve. The selected set of jaws may be arranged to form a plurality of groups of one or more jaws, such as two, three, four, five, six, or more groups of jaws 2, that are evenly or non-evenly spaced circumferentially around the crimping aperture 36 in locations corresponding to the positions of the ventricular anchors 112. Typically, there are at least as many groups of jaws with recessed portions 52 as there are anchors on the prosthetic valve, and in particular embodiments, the number of groups matches the number of anchors 112 on the prosthetic valve. In one implementation, for example, a crimping apparatus is designed to crimp a prosthetic valve having two diametrically opposed ventricular anchors 112 (such as shown in FIGS. 9-11) and therefore can have two groups of one or more jaws having recessed portions 52 on opposing sides of the crimping aperture, such that the recessed portions 52 of each group are sized and positioned to receive a respective ventricular anchor 112 of the prosthetic valve. In another implementation, a crimping apparatus can have four groups of jaws having recessed portions 52 such that recessed portions 52 each of group are sized and positioned to receive a respective anchor 112 of a prosthetic valve having four such ventricular anchors 112.

Figures 12A, 12B:
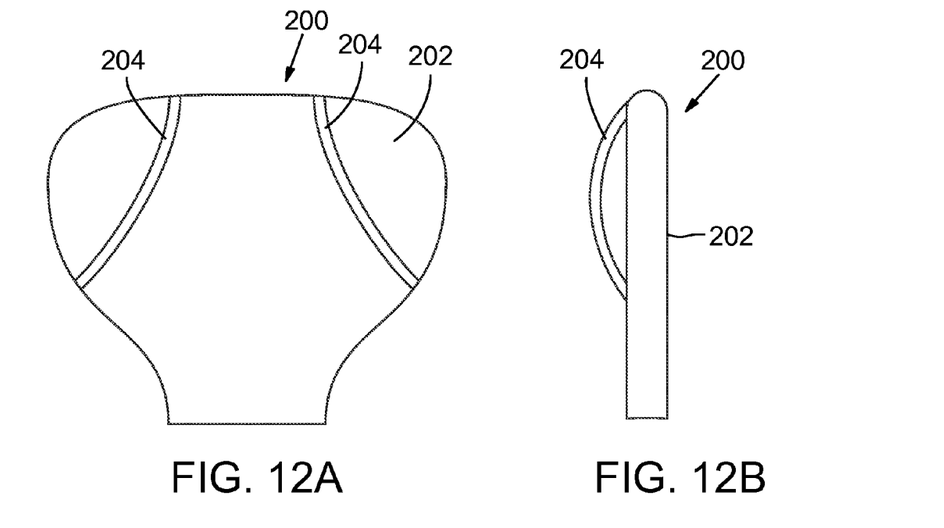
FIGS. 12A, 12B, and 12C are front, side, and top views, respectively, of an exemplary embodiment of a shielding member that can be mounted on the anchor of a prosthetic valve during a crimping process.
Figures 12C, 13:
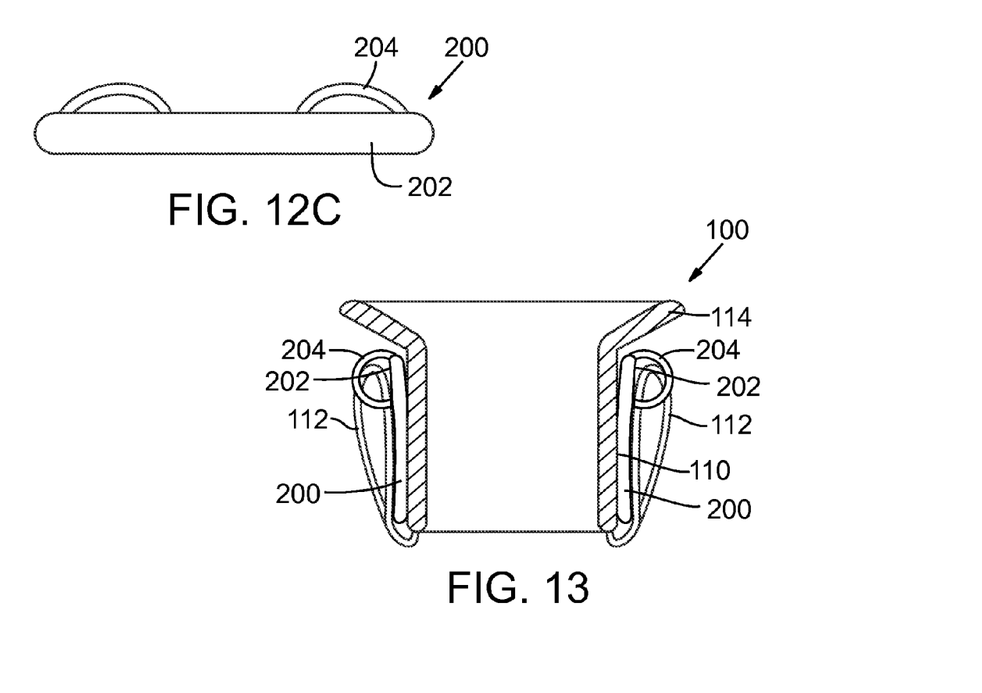
FIG. 13 is a side view of a prosthetic valve having shielding members mounted on the anchors of the prosthetic valve.

FIGS. 12A, 12B, and 12C show an optional accessory that can be used to protect the first anchors 112 from protruding into the spaces between the jaws 2 during the crimping process. In particular, these figures show a shielding member 200 (also referred to as a "sled") that is configured to be mounted on a first anchor 112 of a prosthetic valve and avoid direct contact between the anchor and the jaws 2 to avoid the anchor from protruding into the spaces between the jaws. The shielding member 200 comprises a main body 202 that can have an overall size and shape that corresponds to that of a first anchor 112. The shielding member 200 can further include one or more releasable fasteners such as the illustrated clips 204 that are configured to retain the main body 202 against the inner surface of the first anchor 112. The main body 202 desirably comprises a relatively rigid, low-friction material, such as any of various suitable polymeric materials, including but not limited to, polytetrafluoroethylene (PTFE), polyoxymethylene (POM, for example, Delrin® POM (DuPont, Wilmington, Del.)), or ultra-high-molecular-weight polyethylene (UHMWPE).

FIG. 13 shows shielding members 200 mounted to the anchors 112 of a prosthetic valve 100. As shown, the main body 202 of a shielding member can be placed inside of an anchor 112 and the clips 204 can be placed over the tip of the anchor so as to hold the main body 202 against the inside surface of the anchor adjacent the outer surface of the main body 110 of the prosthetic valve. Thus, when the main body 110 is placed inside the crimping aperture 36 and the anchors 112 are placed within the recessed portions 52 of the jaws, the shielding members 200 contact the inner surfaces 54 of the recessed portions. During the crimping process, the jaws 2 can slide against the shielding members 200, which prevent contact between the anchors and the jaws and prevent the anchors from protruding into the spaces between the jaws, thereby protecting against undesirable deformation of the anchors. The shielding members 200 can be removed from the anchors 112 after the prosthetic valve is removed from the crimping apparatus and before it is loaded into the sheath of a delivery catheter.

Figure 14:
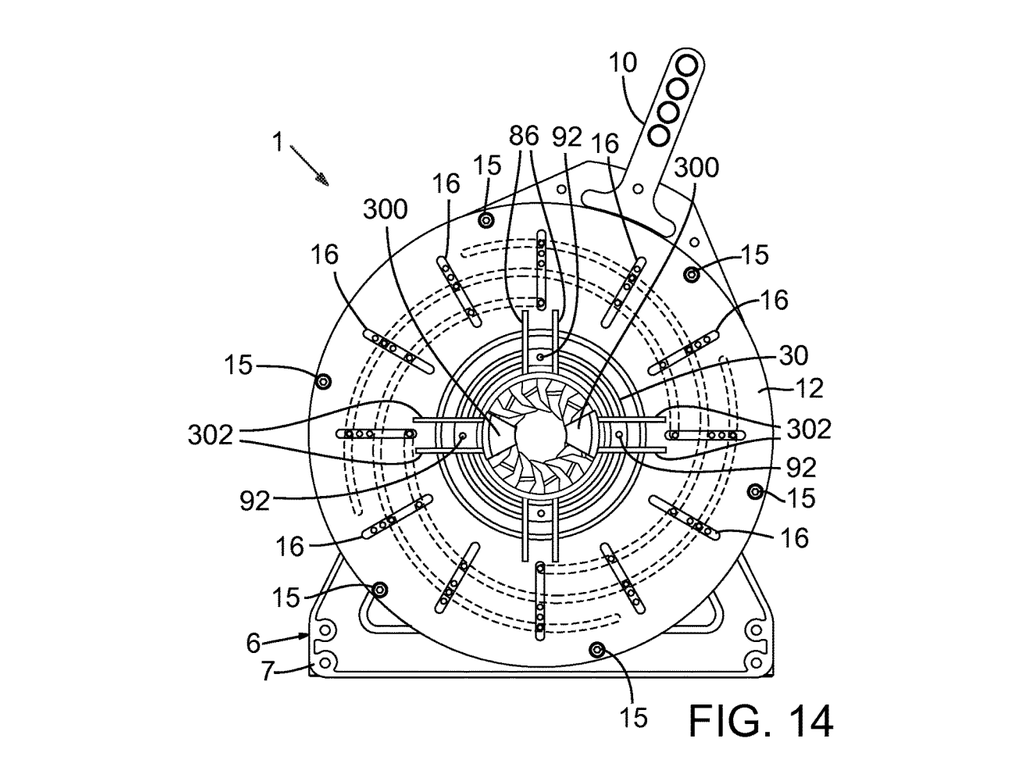
FIG. 14 is a side elevation view of one embodiment of a crimping apparatus having slidable shielding members for supporting the anchors of a prosthetic valve during a crimping process, wherein the jaws are shown in the open position.
Figure 15:
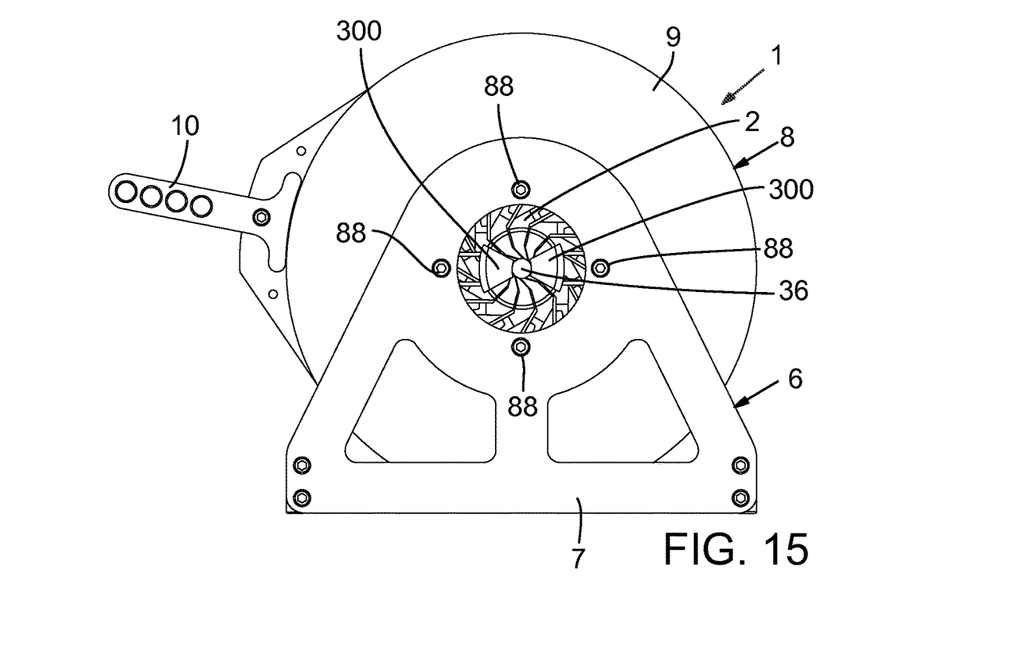
FIG. 15 is a side elevation view of the crimping apparatus of FIG. 14, showing the jaws in the closed position.

Alternatively, or in addition, shielding members can be integrated into or mounted on the crimper mechanism. FIG. 14 shows one exemplary embodiment of a crimping apparatus 1 modified to include shielding members 300 disposed in the recessed portions 52 of the jaws 2. (The near side portion 7 of the stationary frame 6 and the near side portion 9 of outer housing 8 have been removed for clarity.) The shielding members 300 can be operatively coupled to the jaws 2 such that radial movement of the jaws also causes radial movement of the shielding members 300 along respective pairs of rails 302 between a first position when the jaws are open to receive a prosthetic valve (FIG. 14) and a second position when the jaws have been moved radially inwardly to the reduce the size of the crimping aperture (FIG. 15). The shielding members 300 may possess one or more rails which fit into tracks 86 on the inner plate 12, thereby constraining the shielding members and restricting non-radial movement. Radial movement can be accomplished through operative contact with jaws 2 or connection via camming member to the outer housing 8 (not shown). The shielding members 300 desirably are sized and shaped so as to generally correspond to the size and shape of the first anchors 112 of the prosthetic valve to be crimped. In use, the main body 110 of a prosthetic valve can be placed in the crimping aperture 36 and the first anchors 112 can be placed on the shielding members 300. As the main body of the prosthetic valve is crimped, the shielding members 300 support the anchors 112 and prevent them contacting the jaws and protruding into the spaces between the jaws.

The number and position of the slidable shielding members 300 can vary depending on the design of the prosthetic valve to be crimped. In the illustrated embodiment, for example, the crimping apparatus is provided with two shielding members on opposite sides of the crimping aperture 36 for use with a prosthetic valve having two diametrically opposed first anchors (such as shown in FIGS. 9-11). However, FIG. 14 also shows the position of additional tracks 86 allowing for up to four shielding members 300 to be included. In other embodiments, the first anchors of the prosthetic valve are not diametrically opposed, for example, in embodiments comprising three first anchors, and the tracks 86 and shielding members 300 are arranged to reflect the particular geometry of ventricular anchors.

During the crimping process, the struts of the frame 102 are pushed closer together, reducing the size of the openings defined by adjacent struts, and the radial distance between the metal struts and the leaflets 108 decreases. In some instances, portions of the leaflets 108 can slip between the metal struts, which can pinch and cause damage to the leaflet material. Also, leaflet abrasion can occur from the metal struts rubbing against the leaflets.

Figure 16:
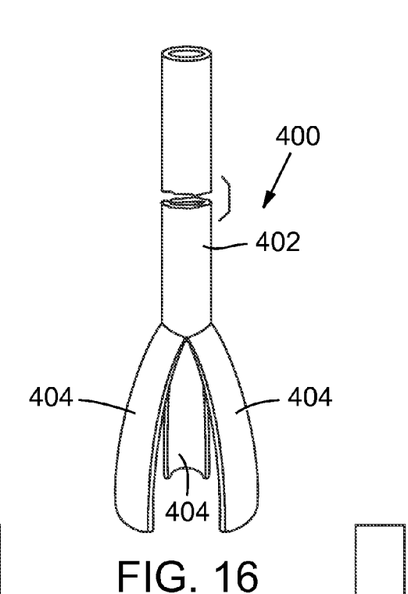
FIG. 16 is a perspective view of a device for protecting the leaflets of a prosthetic valve during crimping, according to one embodiment.

FIG. 16 shows a crimping accessory device or tool 400 that protects the leaflets from damage caused by the metal struts, thereby providing atraumatic crimping of the prosthetic valve. The device 400 in the illustrated configuration comprises a handle in the form of an elongated shaft 402 and one or more shielding members, or fingers, 404 extending from the end of the shaft 402. In the illustrated embodiment, there are three fingers 404, each corresponding to one leaflet of a prosthetic valve having three leaflets 108 (as shown in FIG. 9). In alternative embodiments, the number of fingers can be greater or fewer than three depending upon the number of leaflets present in the prosthetic valve to be crimped. In alternative embodiments, each finger can be connected to a separate shaft so that each finger and shaft functions as a separate tool and one or more of such tools can be used for crimping a prosthetic valve.

The fingers 404 are sized and shaped to be placed in the space between each leaflet 108 and the frame 102 of a prosthetic valve and shield the leaflets from coming into direct contact with the metal struts of the frame as the diameter of the frame is reduced during the crimping process. In some embodiments, the fingers 404 are sized and shaped to cover substantially the entire outer surface of the leaflets 108. In other embodiments, the fingers can be smaller than the leaflets themselves but have sufficient thickness, length and width to prevent leaflet material from creasing and protruding outwardly through the openings of the frame.

Typically, the spaces between the outer surface of each leaflet and the inner surface of the frame are separated by the commissures of the leaflet assembly 104, which form vertical seams extending from the coaptation edges of the leaflets at the inner surface of the frame. It is therefore desirable to have at least one finger for each leaflet of the prosthetic valve so that at least one finger can be easily placed behind each leaflet. In some embodiments, the device 400 can have two or more fingers that are configured to be placed behind a single leaflet. In alternative embodiments, the device 400 can have a single finger 404 configured to extend behind more than one leaflet if the configuration of the leaflet assembly can accommodate the shape of the finger.

The fingers 404 desirably comprise a soft, flexible, resilient, lubricious and/or compressible material, including, but not limited to, natural or synthetic sponge (e.g., polyurethane sponge), a foamed material made of a suitable polymer such as polyurethane or polyethylene, any of various suitable elastomeric materials, such as polyurethane, silicone, polyolefins, polytetrafluoroethylene (PTFE), or a variety of hydrogels, any of various types of natural tissue, such as fixed pericardial tissue, to name a few. In other embodiments, the fingers 404 can comprise inflatable structures (similar to the inflatable balloon of a balloon catheter) that can be inflated with a fluid (a gas or a liquid) prior to use.

Figure 17:
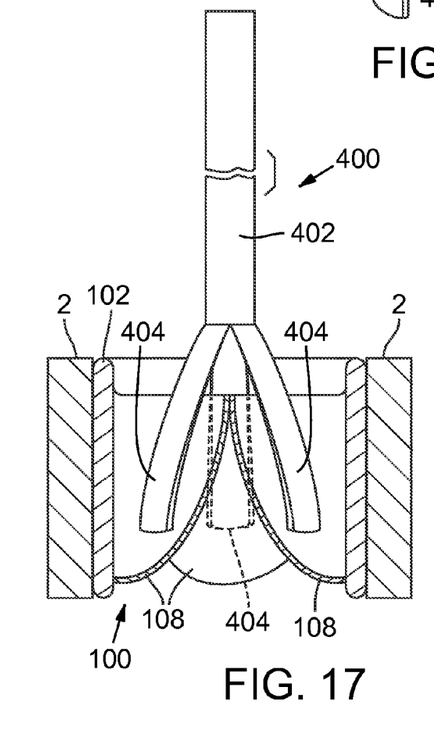
FIG. 17 is a schematic view showing the device of FIG. 16 inserted into a prosthetic valve that is ready to be crimped in a crimping apparatus.
Figure 18:
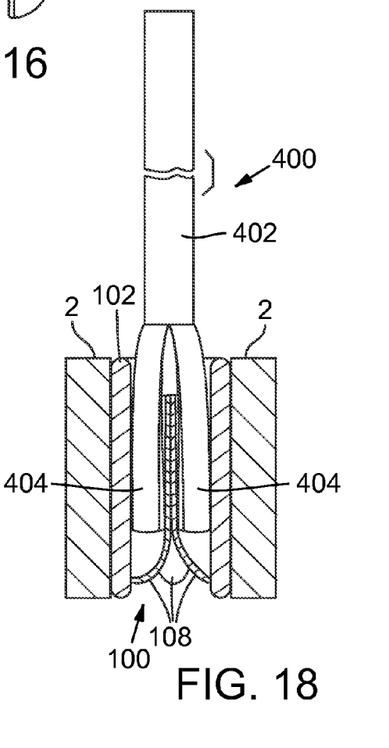
FIG. 18 is a schematic view similar to FIG. 17 showing the prosthetic valve after it has been crimped in a crimping apparatus.

The device 400 can be used when crimping a plastically-expandable or self-expandable prosthetic valve. FIGS. 17 and 18 show use of the device 400 for crimping a prosthetic valve 100. As shown in FIG. 17, each finger 404 is inserted into the space between a respective leaflet 108 and the frame 102 of the prosthetic valve. FIG. 18 shows the prosthetic valve 100 after being fully crimped by the crimping jaws 2. As shown in FIG. 18, the fingers 404 prevent the leaflets 108 from contacting the frame 108, thereby avoiding damage to the leaflets. The fingers 404 can then be removed from the prosthetic valve by simply pulling the device 400 in the axial direction away from the prosthetic valve 100. If the fingers 404 are inflatable, then they can be deflated before removal from the prosthetic valve.

In some embodiments, the prosthetic valve is partially crimped, the device 400 is then removed from the partially crimped prosthetic valve, after which the prosthetic valve is then further crimped to the fully crimped configuration. In such cases, partial crimping of the prosthetic valve with the device 400 is effective to crease/fold the leaflets in such a manner that leaflet material does not protrude through the openings in the frame when the prosthetic valve is further crimped from the partially crimped state to the fully crimped state without the device 400.

In one advantageous feature, crimping devices disclosed herein may be formed of a polymeric material to reduce cost and weight. In addition, due to the efficiency of the construction, the crimping mechanism may be manufactured at a relatively low cost. Accordingly, the crimping mechanism described herein is well-suited for single-use purposes, thus obviating the need for sterilization between uses.

It should be noted that the particular mechanism for crimping prosthetic valves disclosed herein can be structurally modified in various ways while still performing its essential function. For example, in the exemplary embodiment the jaws move radially but are constrained laterally or rotationally. Camming members on the jaws move along radial channels in a fixed plate, while a rotating plate with a spiral camming track provides the moving force. In a reverse configuration, the jaws can rotate while the spiral camming tracks remain stationary. The radial channels can also rotate with the jaws and camming members. The illustrated embodiment is preferred, however, because of the added complexity to the design with rotating jaws. The alternative is mentioned here only to illustrate that structural variations are entirely possible and potentially within the scope of the disclosure.

In addition, it should be noted that the crimping apparatus can be used to crimp prosthetic valves or stents having configurations other than those shown in the drawings. For example, the crimping apparatus can be used to crimp a prosthetic valve having any number of anchors or protruding members that extend from a crimpable main body of the prosthetic valve. Also, the crimping apparatus can be used to crimp a prosthetic valve that does not have any second anchors 114. Moreover, the crimping apparatus can be used to crimp prosthetic valves that are adapted to be implanted in any of the native annulus of the heart. For example, the crimping apparatus can be used to crimp a prosthetic aortic valve having one or more anchors that are configured to be implanted behind the native leaflets of the aortic valve, pulmonary valve, or tricuspid valve. It also should be noted that the protruding members of the prosthetic valve or stent need not be an anchor member and instead can be any portion of the prosthetic device that extends or projects from a compressible body of the prosthetic device. In any case, the protruding members can be placed in the recessed portions of the jaws to avoid application of crimping forces on the protruding members. Further, the crimpable portion of the prosthetic device need not be a cylindrical or tubular body and instead can have any shape or configuration that is crimpable by the jaws.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment, or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims We therefore claim as our invention all that comes within the scope and spirit of these claims.

We claim:

1. A prosthetic valve crimping apparatus for crimping a prosthetic valve comprising a radially expandable and compressible annular body and two or more protruding anchors extending from the body, the apparatus comprising:
    a housing;
    a plurality of circumferentially arranged nesting jaws that are radially movable within the housing, each jaw having an inner end that has a partial crimping surface including a radially innermost surface of the jaw which combines with the same on the other jaws to form a crimping aperture of variable diameter, the crimping aperture defining a central axis;
    a selected set of the jaws each having a front side and a recessed portion in its front side adjacent to its inner end, the radially innermost surface of the jaw and the recessed portion form a wedge shaped finger extending towards the front side, wherein the recessed portions of the selected jaws collectively are configured to receive the anchors of the prosthetic valve when the annular body is positioned within the crimping aperture; and
    an actuator configured to move the jaws radially inwardly to reduce the size of the crimping aperture, thereby radially compressing the annular body of the prosthetic valve;
    wherein the radially innermost surface of each jaw extends from the front side to a back side of the jaw and parallel to the central axis, wherein the recessed portion of each of the selected jaws is defined by a surface that extends from the front side of the jaw toward the back side of the jaw, and—wherein the surface of the recessed portion extends from a forwardmost end of the wedge shaped finger at the front side of the jaw toward the back side of the jaw at an angle from about 5 to about 85 degrees relative to the radially innermost surface and the central axis, and wherein the surface is positioned between the recessed portion and the innermost surface of the jaw.

2. The apparatus of claim 1, wherein the selected set of the jaws comprises all of the jaws.

3. The apparatus of claim 1, wherein the selected set of jaws is less than the plurality of circumferentially arranged nesting jaws, and further wherein the selected set of the jaws comprises a plurality of groups of jaws that are evenly spaced circumferentially around the crimping aperture.

4. The apparatus of claim 1, wherein the selected set of jaws is less than the plurality of circumferentially arranged nesting jaws, and further wherein the selected set of the jaws comprises two groups of jaws on opposing sides of the crimping aperture.

5. The apparatus of claim 1, wherein the angle is between from about 10 to about 70 degrees.

6. The apparatus of claim 1, further comprising a plurality of slidable shielding members disposed within the recessed portions of the selected jaws, each shielding member comprising a fastener to releasably engage one of the anchors of the prosthetic valve when the annular body is positioned within the crimping aperture, each shielding member being configured to move radially inwardly when the actuator is actuated to move the jaws radially inwardly.

7. The apparatus of claim 6, wherein the plurality of shielding members comprise two shielding members on diametrically opposing sides of the crimping aperture.

8. A prosthetic valve crimping apparatus for crimping a prosthetic valve comprising a radially expandable and compressible annular body and two or more protruding anchors extending from the body, the apparatus comprising:

- a housing;
- a plurality of circumferentially arranged nesting jaws that are radially movable within the housing, each jaw having an inner end that has a partial crimping surface including a radially innermost surface of the jaw which combines with the same on the other jaws to form a crimping aperture of variable diameter;
- a selected set of the jaws each having a front side and a recessed portion in its front side adjacent to its inner end, the radially innermost surface of the jaw and the recessed portion form a wedge shaped finger extending towards the front side, wherein the recessed portions of the selected jaws collectively are configured to receive the anchors of the prosthetic valve when the annular body is positioned within the crimping aperture, further wherein the selected set of jaws is less than the plurality of circumferentially arranged nesting jaws; and
- an actuator configured to move the jaws radially inwardly to reduce the size of the crimping aperture, thereby radially compressing the annular body of the prosthetic valve.

9. The apparatus of claim 8, wherein the selected set of the jaws comprises a plurality of groups of jaws that are evenly spaced circumferentially around the crimping aperture.

10. The apparatus of claim 8, wherein the selected set of the jaws comprises two groups of jaws on opposing sides of the crimping aperture.

11. The apparatus of claim 8, wherein the recessed portion of each of the selected jaws is defined by a surface that extends from the front side of the jaw toward back side of the jaw, and wherein an angle between the radially innermost surface of the jaw and the surface of the recessed portion is between from about 5 to about 85 degrees.

12. The apparatus of claim 11, wherein the angle is between from about 10 to about 70 degrees.

13. The apparatus of claim 8, further comprising a plurality of slidable shielding members disposed within the recessed portions of the selected jaws, each shielding member comprising a fastener to releasably engage one of the anchors of the prosthetic valve when the annular body is positioned within the crimping aperture, each shielding member being configured to move radially inwardly when the actuator is actuated to move the jaws radially inwardly.

14. The apparatus of claim 13, wherein the plurality of shielding members comprise two shielding members on diametrically opposing sides of the crimping aperture.

15. A prosthetic valve crimping apparatus for crimping a prosthetic valve comprising a radially expandable and compressible annular body and two or more protruding anchors extending from the body, the apparatus comprising:

- a housing;
- a plurality of circumferentially arranged nesting jaws that are radially movable within the housing, each jaw having an inner end that has a partial crimping surface including a radially innermost surface of the jaw which combines with the same on the other jaws to form a crimping aperture of variable diameter;
- a selected set of the jaws each having a front side and a recessed portion in its front side adjacent to its inner end, wherein the recessed portions of the selected jaws collectively are configured to receive the anchors of the prosthetic valve when the annular body is positioned within the crimping aperture, further wherein the radially innermost surface of the jaw and the recessed portion form a wedge shaped finger extending towards the front side, the wedge shaped finger locatable between the annular body and the anchors; and
- an actuator configured to move the jaws radially inwardly to reduce the size of the crimping aperture, thereby radially compressing the annular body of the prosthetic valve, wherein the selected set of the jaws is less than the plurality of circumferentially arranged nesting jaws.

16. The apparatus of claim 15, wherein the selected set of the jaws comprises a plurality of groups of jaws that are evenly spaced circumferentially around the crimping aperture.

17. The apparatus of claim 15, wherein the selected set of the jaws comprises two groups of jaws on opposing sides of the crimping aperture.

18. The apparatus of claim 15, wherein the recessed portion of each of the selected jaws is defined by a surface that extends from the front side of the jaw toward back side of the jaw, and wherein an angle between the radially innermost surface of the jaw and the surface of the recessed portion is between from about 5 to about 85 degrees.

19. The apparatus of claim 18, wherein the angle is between from about 10 to about 70 degrees.

\* \* \* \* \*